United States Patent  
Mott

(10) Patent No.: US 6,270,469 B1  
(45) Date of Patent: *Aug. 7, 2001

(54) ABDOMINAL POSTOPERATIVE BINDER AND METHOD OF USE

(76) Inventor: George E. Mott, 10619 Tower Oaks, Houston, TX (US) 77070

(*) Notice: Subject to any disclaimer, the term of this patent is extended or adjusted under 35 U.S.C. 154(b) by 0 days.

This patent is subject to a terminal disclaimer.

(21) Appl. No.: 09/599,853

(22) Filed: Jun. 23, 2000

Related U.S. Application Data

(63) Continuation-in-part of application No. 08/856,813, filed on May 15, 1997, now Pat. No. 6,080,125.

(51) Int. Cl.[7] .................................................. A61F 13/00
(52) U.S. Cl. ........................ 602/61; 602/60; 602/67; 602/75; 128/96.1; 128/99.1; 128/100.1; 450/140; 2/401
(58) Field of Search ................................. 602/60–61, 67, 602/75; 128/96.1, 99.1, 100.1; 450/140; 2/401

(56) References Cited

U.S. PATENT DOCUMENTS

| | | | |
|---|---|---|---|
| 79,994 | * | 7/1868 | Lindley . |
| 156,050 | * | 10/1874 | Washburn . |
| 647,551 | * | 4/1900 | Bain . |
| 2,355,740 | * | 8/1944 | McNees . |
| 2,605,762 | * | 8/1952 | Balisterieri . |
| 2,684,673 | * | 7/1954 | Lerman . |
| 3,393,674 | * | 7/1968 | Nelkin . |
| 3,895,629 | * | 7/1975 | Snyder . |
| 4,059,103 | * | 11/1977 | Glaser . |
| 4,446,575 | * | 5/1984 | Davis . |
| 4,932,079 | * | 6/1990 | Bridgewater . |
| 5,003,972 | * | 4/1991 | Kestler . |
| 6,080,125 | * | 6/2000 | Nott . |

* cited by examiner

Primary Examiner—Mickey Yu  
Assistant Examiner—Lalita M Hamilton  
(74) Attorney, Agent, or Firm—Arthur M. Dula

(57) ABSTRACT

The invention is a postoperative binder and method of use. The binder is made of relatively inelastic material that is cut to fit the patient and held in place by a plurality of tails fastened with Velcro® binders. The present invention uses mechanical, rather than elastic, compression. Mechanical loads are carried over the iliac crest, by hooking the tails of the binder over the iliac crest and then bifurcating the tails for attachment to the abdominal portion of the binder. The present invention provides support of lower abdominal tissue, especially near the genitals and in the area of the peritoneum. The invention is also a method of preventing post-operative wound infection, reducing incidence of seroma and hematoma formation and wound separation while reducing pain and the need for pain medication by passing a relatively inelastic abdominal binder over the patient's iliac crest and abdomen to place the binder in tension so as to provide a greater than 180 degree radius of compression to the wound.

7 Claims, 4 Drawing Sheets

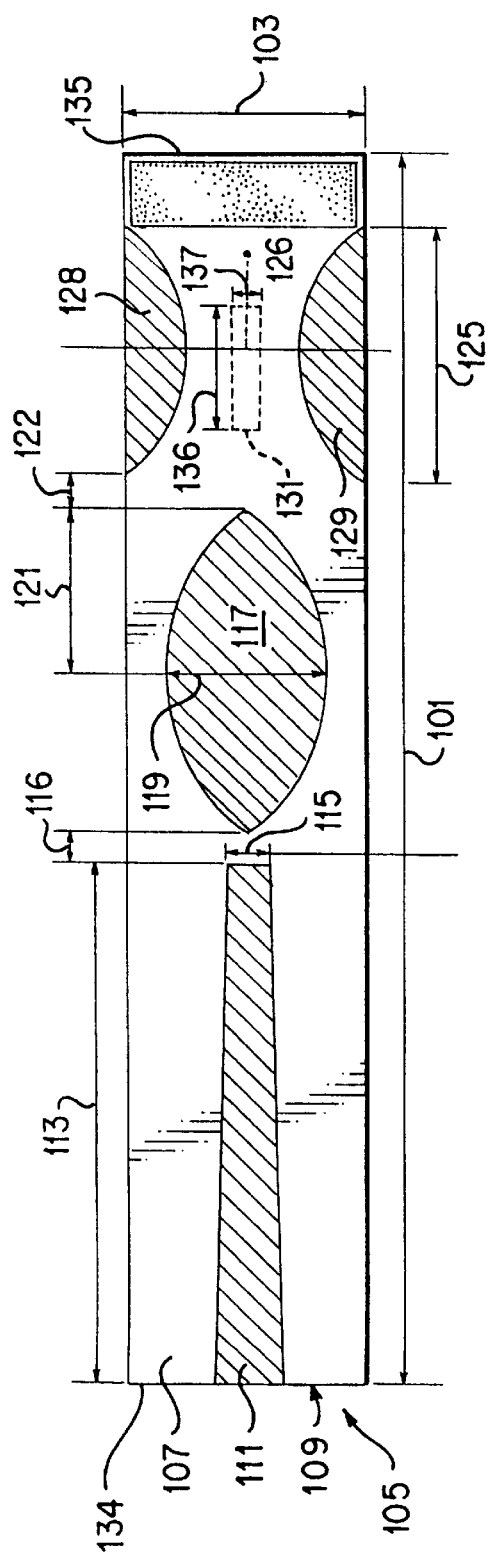
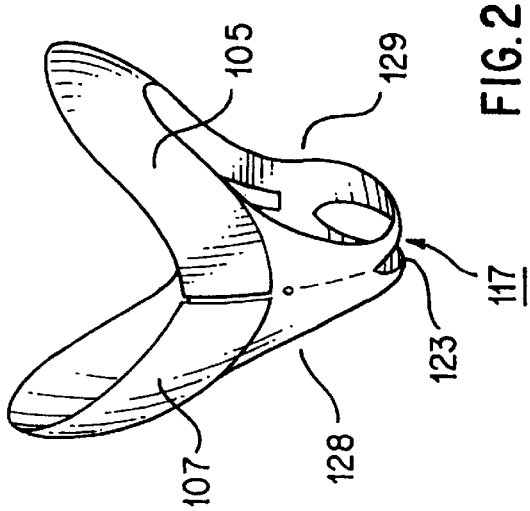

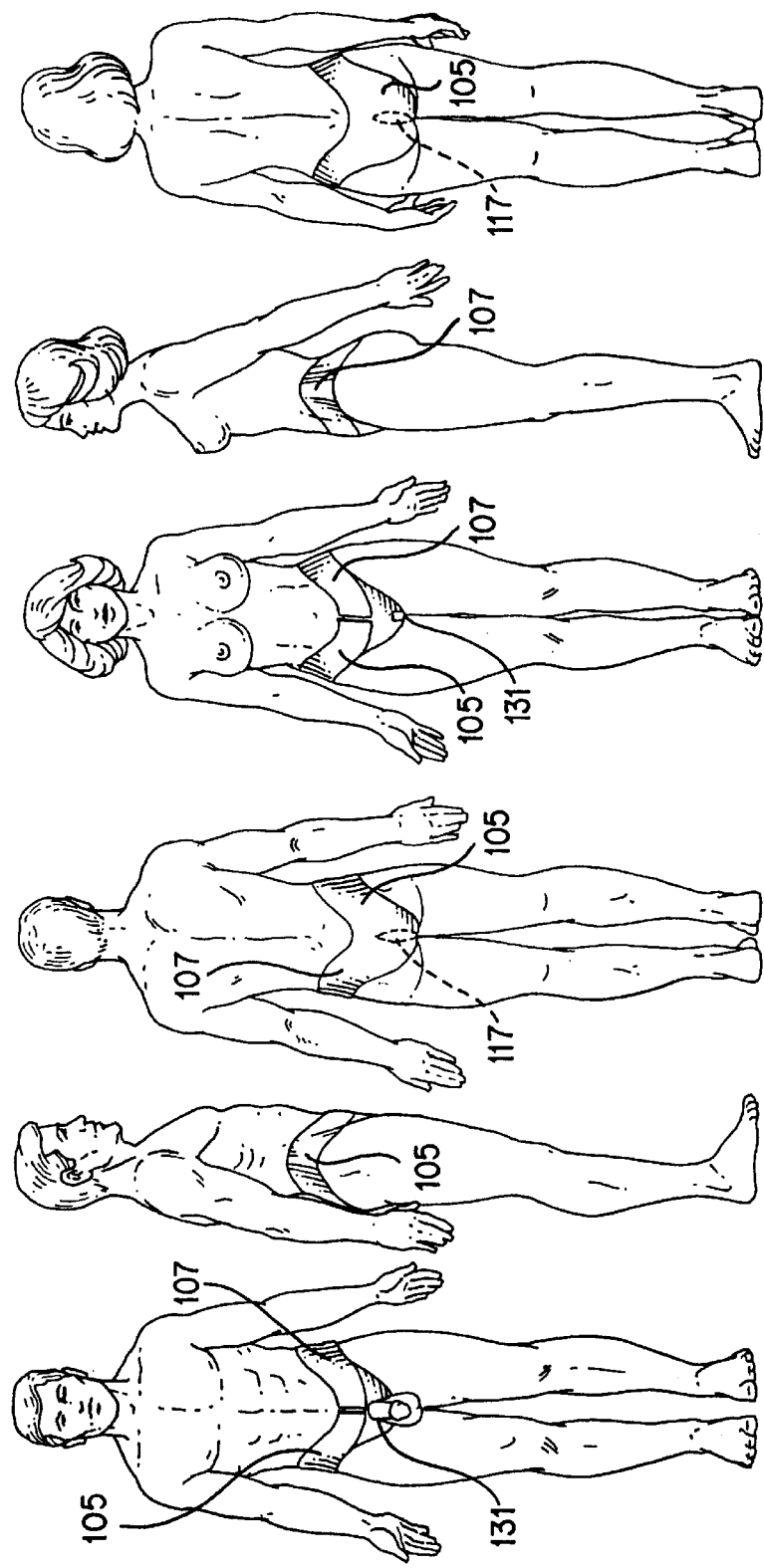

ABDOMINAL POSTOPERATIVE BINDER AND METHOD OF USE

RELATED APPLICATIONS

This is a continuation-in-part application of Ser. No. 08/856,813 that was filed on May 15, 1997 and issued as U.S. Pat. No. 6,080,125 on Jun. 27. 2000.

BACKGROUND OF THE INVENTION

1. Field of the Invention

The invention is an improvement in medical support garments. More specifically the present invention is a postoperative support binder for patient use after abdominal surgery to control pain, edema and infection, whereby postoperative complications are reduced and recovery time and postoperative mobility of patients is improved.

2. Background of the Prior Art

Patients who have undergone aesthetic or reconstructive surgery of the abdomen, genitals or pelvis are likely candidates for some form of complications during the recovery period. Typical complications are atelectasis, hypostatic pneumonia, phlebitis and pulmonary complications. Clinical evidence indicates that 20 to 40 percent of patients will experience pulmonary complications (Bartlett, Robert H. et al., Respiratory Maneuvers to Prevent Post-Operative Pulmonary Complications, JAMA, Vol. 224, No. 7, (1973). Thus it is important that the rehabilitation program encourage and develop the return of respiratory efficiency.

Early ambulation is a key factor in helping the patient reestablish his normal physiology and preventing or minimizing postoperative complications. Ambulation hastens muscle redevelopment, wound healing (Brunner, Lillian Sholtis, et al., The Textbook of Medical Surgical Nursing (Second Edition, Lippincott, Philadelphia, 1978) p. 134.) and the return of vital lung capacity (Ali, J. and Khan, T. A., The Comparative Effects of Muscle Transection and Median Upper Abdominal Incision on Post Operative Pulmonary Function, Surgery, Gynecology & Obstetrics, Vol. 148, No. 6, (1979)).

The prior art teaches the use of binders or girdles that use the elastic properties of fiber to provide abdominal support, such as U.S. Pat. No. 5,571,039, issued to Ford in 1994. This abdominal support comprises a plurality of webs having therein elastic fibers, said web forming the girdle that fits around at least a portion of the abdomen, hips and buttocks of the patient. Another example is the waist support and hip girdle taught by U.S. Pat. No. 3,783,879 issued to Stalder in 1971, which teaches use of a knitted elastic fabric with an open mesh.

The best prior art known to the present inventor is the commercial postoperative binders sold by the Veronique Compression Wear company of San Leandro, Calif.; and the Dale® Abdominal Binder, sold by Dale Medical. All of the prior art known to the inventor depends primarily on the elastic properties of the material forming the binder to provide the compression. The use of such postoperative compression clothing is a well-established medical practice. Abdominal binders have been assigned Medicare/Medicaid reimbursement codes L0960 or A4465.

The prior art has a problem. The prior art uses the stretch of an elastic fiber to provide compression, the garments tend to roll, 'rope' or bunch up. Also elastic force is insufficient to control edema. They provide the least pressure where there is swelling, as elastic conforms to the body shape of the patient.

BRIEF DESCRIPTION OF THE INVENTION

The present invention is a postoperative binder made of relatively inelastic material that is cut to fit the patient and held in place by Velcro®. The present invention uses mechanical, rather than elastic, compression in this relatively inelastic material. Mechanical loads are carried near or on the hip joint, either by physically hooking the binder over the hips or attaching it to an elastic band that rides on or above the patient's hips. The present invention provides greater mechanical support to lower abdominal tissue, especially near genitals and in the area of the peritoneum, than is possible using prior art elastic binders. This solves the problem of fluid tissue water retention and long healing times that are not answered by existing designs.

The invention's special industrial utility comprises:

a. Obesity surgery: male or female
b. Postoperative wound care: especially for diabetic, immune compromised (AIDS) or vascular insufficiency.
c. Military wounds/trauma: especially crushing injury, blast injury, gun shot, blunt trauma (car wreck), military field stabilization to control bleeding in lower abdomen and/or upper portion of lower extremities.
d. Penile surgery: penile augmentation, penile amputation (cancer); penile reconstruction.
e. Vaginal delivery, caesarian section wounds.
f. General surgery: hernia repair, abdominal and/or rectal cancer resection, orthopedic surgery, total hip replacement (support for rotary abductor box); hip nailing.
g. Hyperbaric care: scrotal lymph edema, section wounds in obese patients or those who are immune or vascularly compromised; difficult wound healing.
h. Sex change surgery For the state of the art please see:

1. Weiss, E. B., Dale Combo Abdominal Binders—A Study in a Post-Operative Setting, (Independent clinical study conducted at St. Vincent's Hospital, Worcester, Mass. Date available on request.)
2. Khan, T. A., Serrette, C., and Ali, J., The Effect of Abdominal Binders on Postoperative Pulmonary Function, Infections in Surgery, Vol. 2., No.1 L pp. 875–881, November 1983.
3. Finn, Kathleen, How's Your Post-Op Ambulation Technique? R.N., Vol. 42, page 9.

Abdominal Surgery in General

After open abdominal surgery, the patient may avoid the very activities that can help restore normal pulmonary function and muscle redevelopment. These activities are deep breathing, coughing, and ambulation. To the patient even the thought of sitting up or getting out of bed may seem forbidding and coughing can be a frightening experience. Under these circumstances, the patient needs instruction and direct physical assistance in splinting coughs, maneuvering in and out of bed, breathing, and walking erect.

Patients with abdominal incisions tend to hunch over in an attempt to splint the wound, and need frequent reminders to straighten up. It may help to explain that good posture promotes healing by exerting just enough tension on abdominal muscles to strengthen them without disrupting the wound. Slouching, on the other hand, throws the patient off balance, discourages deep breathing, and strains back muscles.

Frequently, when a patient wakes up in recovery he inadvertently coughs and immediately discovers how painful the wound is. Thereafter, the patient may intentionally or subconsciously suppress future coughs in order to minimize the painful experience. This is of course counter to the prescribed necessity of initiating deep breathing, coughing and ambulation. The nurse in the unit may teach the patient how to splint the wound with a pillow to lessen the pain. But often, when the nurse leaves, the patient puts down the pillow and fails to continue his or her instructions. Application of the binder allows the patient to perform required breathing and other activities in a manner that is more comfortable, less painful and without supervision.

The present invention helps to overcome the patient's reluctance to engage in therapeutic activities. The present invention used with Velcro® fasteners is more effective and easier to apply than the many-tailed scultetus binder that fastened with safety pins.

Gall Bladder Surgery

Patients recovering from traditional gall bladder surgery are especially prone to pulmonary complications as are all patients with upper abdominal incisions. It is recommended that these postoperative patients be gotten out of bed as soon as possible to prevent pulmonary complications. The present invention can insure greater comfort while aiding and encouraging coughing and deep breathing.

Bariatric Procedures

In surgical treatments of the morbidly obese such as vertical banded gastroplasty or gastric resection, an abdominal binder has many applications for the patient in the early postoperative period. It lessens the danger of pulmonary complications by encouraging deep breathing and coughing and helps to counteract the patient's natural tendency toward shallow breathing. The present invention makes it easier for the patient to move and turn comfortably. It allows earlier ambulation thus promoting increased respiratory exchange. The abdominal binder, supporting the incision, helps to guard against wound evisceration and infection during the healing process (The Lippincott Manual of Nursing Practice (Lippincott, Philadelphia, 1974) p. 394.) It also helps to control distention and prevent herniation of the peritoneum, as well as unwanted fluid buildup.

Plastic and Cosmetic Surgical Procedures

The use and application of binders to assist postoperative activity for 2 to 4 weeks after abdominal liposuction/lipectomy and/or abdominoplasty is common and well documented. (Newman, Julius, M.D., Bergermeister, Herman, M.D., Golshai, Mohammad, M.D., Closed Lipo-Sweep Abdominal Liposuction, The American Journal of Cosmetic Surgery, Vol. 8, No. 1 1991.) Unlike the prior art binders or elastic garments, the present invention is constructed of relatively inelastic material that facilitates patient movement, yet will not "ride up", roll, or rope during use.

The construction of the present invention allows the surgeon to cut holes anywhere on the binder to allow for drainage tubes without the material running or fraying. The present invention can be used to secure the taping that is used to help bind the sections of skin together to prevent splitting of the incision, and promote scarring. (Matarasso, Alan, M.D, Abdominolipoplasty: A System of Classification and Treatment for Combined Abdominoplasty and Suction-Assisted Lipectomy, Aesthetic Plastic Surgery, 15111–121 1991.)

Use of the present invention also encourages post-op movement to prevent muscular atrophy and fluid build-up (seroma) which is often associated with abdorninoplasty and extensive suction lipectomy.

Hernia Repair

In addition to good general postoperative care, the nurse, in caring for the patient who has had an operation for a hernia, should prevent tension on the newly repaired tissues. If a cough occurs, medications are usually prescribed to depress the cough reflex. They should be given as ordered to prevent paroxysms of coughing and subsequent strain on the repair. (Shaefer, Kathleen Newton, et al., Medical Surgical Nursing (CV Mosby, St. Louis, 1971) p. 615. Use of the present invention can serve to support the incision area, lessen the pain of coughing, and promote the healing process.

Obstetrics and Gynecology

General

In certain post-hysterectomy cases where a tumor has been large enough to cause a marked relaxation of the abdominal wall, wearing an abdominal binder is recommended after surgery. Following an abdominal hysterectomy, the patient may require additional support of the incised abdominal musculature, particularly during ambulation and especially if her abdomen is large or its musculature weak. The present invention can be used to provide the additional support during the healing process. (Nursing Care of the Patient with Medical Surgical Disorders (McGraw-Hill, New York, 1971) p.124.

The post-operative nursing care after cystectomy is similar to that for abdominal surgery, except for one particular. The marked decrease in intra-abdominal pressure incidental to the removal of a large cyst often leads to considerable abdominal distention. This complication may be prevented to some extent by the application of a pad or abdominal binder.

Cesarean Section

After cesarean section, as with other types of open abdominal surgery, the patient will find an increased level of confidence in sitting up, ambulating, and resuming other post-op activities if the binder is used. While the incision of the procedure does not cut through muscle or compromise the diaphragm, the incision is nevertheless long and painful. The present invention will enable the patient to move freely and perform any prescribed incentive breathing program, without the fear of the sutures breaking, or the wound eviscerating.

Post-Partum

Following delivery, a woman may be advised by her physician to use a binder if her abdomen is unusually flabby or pendulous, and, if her musculature has been weakened by the pregnancy (Henderson, Virginia and Nite, Gladys, Principles & Practice of Nursing (Sixth Edition, Macmillan, New York 1978) p. 1442.) This is particularly important psychologically if the woman believes she would be more comfortable with some support. The present invention provides added encouragement needed when ambulation is prescribed, and muscle redevelopment will proceed normally to overcome the problem. When the woman is ambulatory, the use of the present invention is preferable to a scultetus binder or other prior art compression clothing because it will stay in place and offer overall support as she moves about.

Urological Procedures

For the patient after kidney or bladder surgery, turning, deep breathing, and coughing are extremely important activities to perform in order to minimize the possibility of atelectasis and pneumonia. Such activities are very painful because of the proximity of the incision to the diaphragm. Pain medication, administered with sufficient time for the narcotic effect to take hold, and the application of the present invention will allow the patient to cough and do deep breathing exercises more effectively and efficiently.

BRIEF DESCRIPTION OF THE DRAWINGS

FIG. 1 is a plane view of the form of the present invention, laid flat;

FIG. 2 is an isometric view of the present invention as it is used on a patient;

FIGS. 3a, 3b and 3c show the front, side and back views, respectively, of the present invention on a male patient;

FIGS. 4a, 4b and 4c show the front, side and back views, respectively, of the present invention on a female patient;

DESCRIPTION OF THE PREFERRED EMBODIMENT OF THE INVENTION

Figure 5:
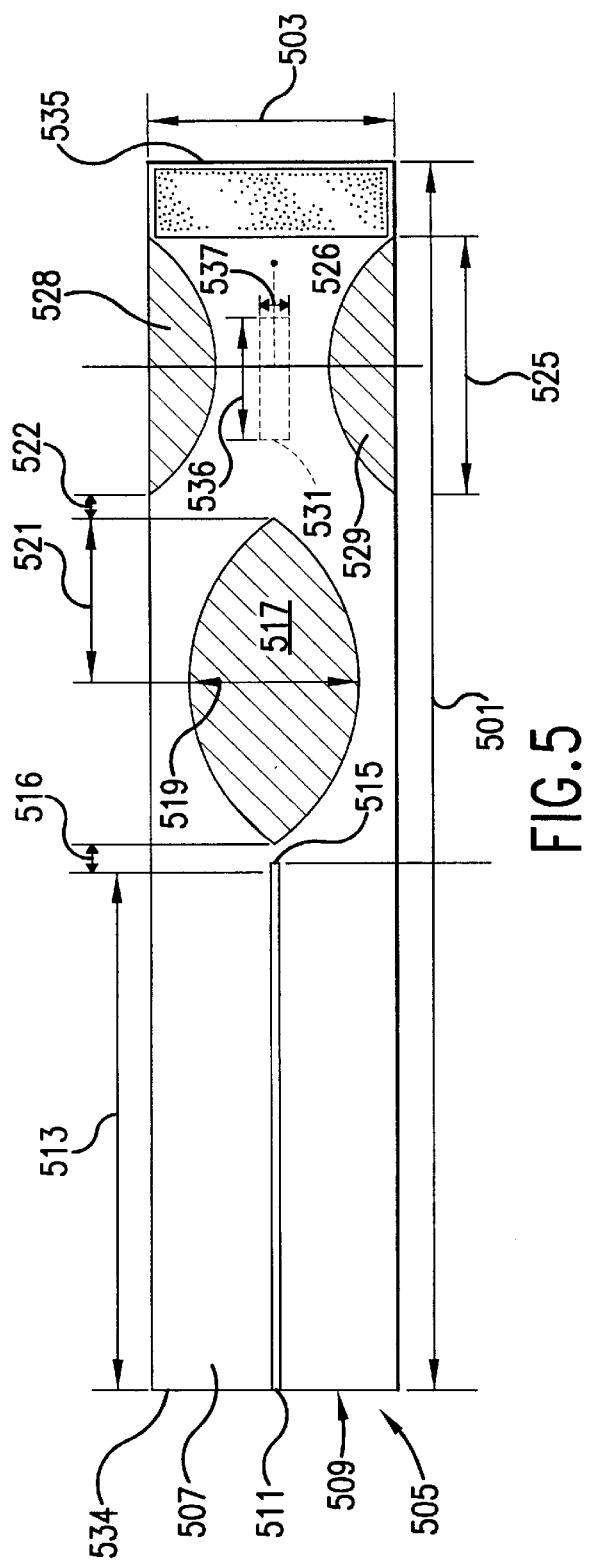
FIG. 5 is a plain view of the embodiment of the present invention that uses a knife cut to separate the two tails, laid flat.

In FIG. 1, a generally rectangular sheet of relatively inelastic material, such as commercial Neoprene®, has a length 101 and a width 103 which are chosen to be generally fitting to the majority of patients. The structure of the binder taught by the present invention is defined by cutting this rectangular sheet to fit the patient, as will be further discussed below.

At a tail end 109 of the sheet a rectangular tapering cutout 111 is made that defines a first leg or tail 105 and a second leg or tail 107. This cut has a tapering width 115 and a length 113, as shown in FIG. 1.

An uncut length 116 of the sheet separates rectangular cut out 111 from a football shaped cut out 117, which has a minor axis 119 and a major semi axis 121. This football shaped cut out section is separated by uncut section 122 from two curve shaped side cut outs 128 and 129 positioned on the left and right edges of the sheet, respectively, which are opposite one another on the sheet. These cut outs 128 and 129 have a length 125 and a greatest width 126. Between cut outs 128 and 129 is a rectangular cut out 131, having a length 136 which is greater than its width 137.

A cut out end 134 opposite the tale end of the sheet is covered with Velcro® fastener 135, whereby ends of tails 105 and 107 removably attaches to said cutout end of said sheet by means of Velcro® fasteners.

The size of the sheet which forms the binder taught by the present invention is selected to match the size of the patient to whom it will be fitted and the cut outs defined above are sized by cutting them to fit the shape of the individual patient.

The binder taught by the present invention may be made of any material that is flexible and relatively inelastic.

FIG. 2 shows an isometric view of the binder taught by the present invention. In FIG. 2 the same structures have the same numbers as in FIG. 1, described above. As shown in FIG. 2, cut out 117 defines an anal opening in the binder. Cut outs 128 and 129 define leg openings, together with tails 105 and 107. End 135 of the binder is shown under and attached to the ends of tails 105 and 107.

FIGS. 3a, 3b and 3c show the front, side and rear view of the binder taught by the present invention on a male patient. In these figures similar numbers as in FIG. 1 denotes similar structures. These views are presented to show how the invention's tails 105 and 107, each having a length 113, ride over the hips of the patient such that the mechanical load maintained by the binder on the patient are carried by the hip bones. If the patient is obese, the present invention may be affixed to an elastic band, not shown, that rides around the patient's hips. Such band holds the invention on the patient, but its elastic property does not provide compression, which is inelasticly provided mechanically by the invention. This figure also shows how the penis of the male patient protrudes through the opening 131 of the invention. This is important because the penile and anal opening of the invention, as they are individually sized and fitted to each patient, allow the binder taught by the present invention to be worn during the entire post operative period.

FIGS. 4a, 4b and 4c show the present invention on a female patient.

FIG. 5 shows an embodiment of the present invention wherein the tails of the invention are separated by a knife cut rather that being spaced apart by a tapering rectangular cutout. In FIG. 5, a generally rectangular sheet of relatively inelastic material, such as commercial Neoprene®, has a length 501 and a width 503 which are chosen to be generally fitting to the majority of patients. The structure of the binder taught by the present invention is defined by cutting this rectangular sheet to fit the patient, as will be further discussed below.

At a tail end 509 of the sheet a rectangular a knife cut 111 is made in the binder material. This bifurcates the length 513 of the binder into a first leg or tails 105 and a second leg or tail 107. This cut has a tapering almost no width, as shown in FIG. 5.

An uncut length 516 of the sheet separates knife cut 511 from a football shaped cut out 517, which has a minor axis 519 and a major semi axis 521. This football shaped cut out section is separated by uncut section 522 from two curve shaped side cut outs 528 and 529 positioned on the left and right edges of the sheet, respectively, which are opposite one another on the sheet. These cut outs 528 and 529 have a length 525 and a greatest width 526. Between cut outs 528 and 529 is there may be a rectangular cut out 531, having a length 536 which is greater than its width 537.

A cut out end 534 opposite the tale end of the sheet is covered with Velcro® fastener 535, whereby ends of tails 505 and 507 may be removably attached to said cutout end of said sheet by means of Velcro® fasteners. The means for attachment may be Velcro®, hooks and eyes, snaps, or even safety pins. In the preferred embodiment of the present invention one side of the Neoprene® binder material is covered with terry cloth having a weave such that it will grippingly engage the hooks of the Velcro® fasteners.

The size of the sheet which forms the binder taught by the present invention is selected to match the size of the patient to whom it will be fitted and the cut outs defined above are sized by cutting them to fit the shape of the individual patient.

The binder taught by the present invention may be made of any material that is flexible and relatively inelastic. In the preferred embodiment of the present invention, the material used is similar to the material used to make Neoprene® wet suits that are used for SCUBA diving. This material is anisotropic with respect to its ability to stretch. In the present invention this quality provides a relatively inelastic material that stretches more in the length than in the width. This property allows the binder taught by the present invention to stretch over the iliac crest of the patient, while the lack of ability to stretch along the binder's width places compression on the patient's abdomen and genital area.

Figure 6:
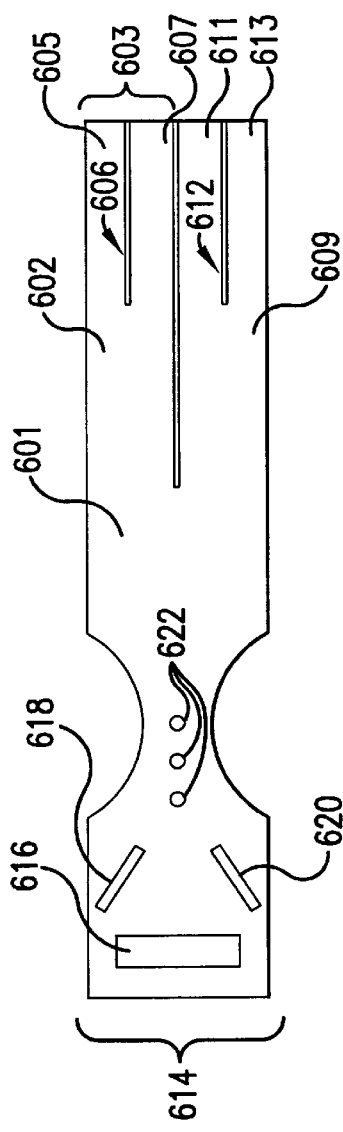
FIG. 6 is a plain view of the embodiment of the present invention for use on female patients wherein the two tails of the invention are bifurcated into four smaller tails.

FIG. 6 shows an embodiment of the present invention wherein binder 601 has two tails 603 and 609 that are separated by a knife cut 602, as was described in FIG. 5 above. In this embodiment each of the tails is again bifurcated along a portion of its length to form four shorter tails. Tail 603 is bifurcated into short tails 605 and 607 by knife cut 606. Tail 609 is bifurcated into short tails 611 and 613 by knife cut 612.

At end 614 of binder 601 the Velcro® fastener 616, which was taught in the embodiment of the invention described in FIGS. 1 and 5, above, is supplemented with two diagonal Velcro® fastener strips, 618 and 620 that are space apart on the right and left sides of the binder, respectively.

FIG. 6 also shows a plurality of relatively small holes 622 placed on in the binder section that will be proximate the genital area of a female patient. The purpose of these holes is to allow ventilation to lessen the probability of the occurrence of yeast infections during the time the binder is worn by a female patient and to allow passage of catheter tubes. For a male patient the holes would be a slit adapted to allow passage of the patient's penis and scrotum, as is shown in FIG. 1, above.

As with all embodiments of the present invention, the embodiment shown in FIG. 6 has a plurality of tails that pass above the iliac crest of the patient and are removable fixed to that part of the binder that covers the patient's abdomen, thereby holding the patient's abdomen in compression. This embodiment of the invention teaches the use of four small tails, two of which, 605 an 613, attach to Velcro® fastener 616 while the other two small tails 607 and 611 attach to the two diagonal Velcro® fasteners 618 and 620, respectively. This will be shown in more detail in FIGS. 7A and 7B below. This has the effect of increasing the radius of compression, i.e. the number of degrees of the patient's abdomen that the binder compresses (measured from above the iliac crest, around the abdomen, to above the other iliac crest) from the about 180 degrees that is possible with two tails, to a radius of compression of about 270 degrees.

Figure 7A:
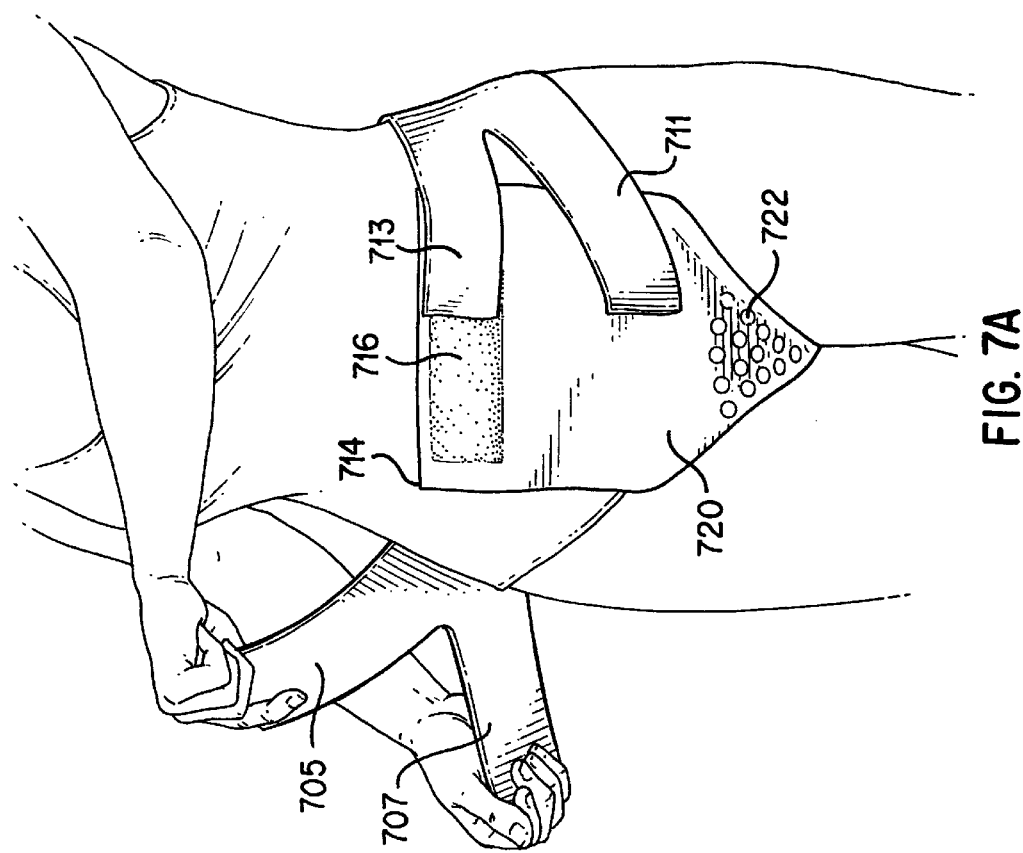
FIG. 7A shows the embodiment of FIG. 6 being as it is being put on by a female patient over her illic crest.

FIG. 7A shows a female patient putting on the abdominal binder taught by the embodiment of the present invention shown in FIG. 6. In this FIG. 7A similar number define similar structures to FIG. 6.

Figure 7B:
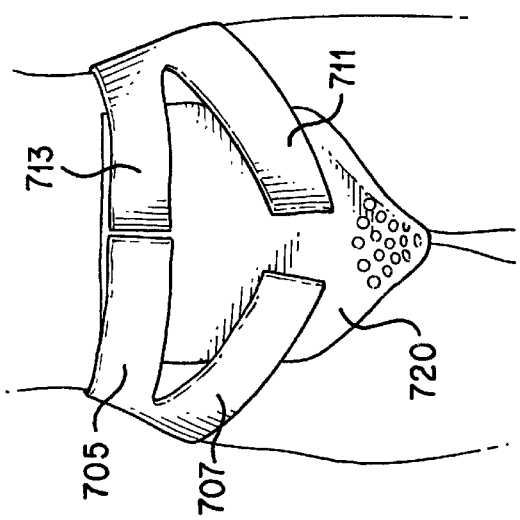
FIG. 7B shows the placement of the bifurcated tails of the invention on the front of the abdomen of a patient.

In FIG. 7A the patient has put binder front 714 on to cover her abdomen with the binder going between her legs and having plurality of small holes 722 proximate her genital region. Small tail 713 is shown fixed by its terry cloth backing to the left side of Velcro® fastener strip 716. Small tail 711 is shown attached by its terry cloth backing to the diagonal Velcro® fastener strip on the left side of the binder, which is not shown because it is covered by tail 711. The patient is shown stretching the anisotropic material of the binder over her iliac crest by pulling small tails 705 and 707 up and over her iliac crest. This places the binder in compression over her abdomen and genital area. FIG. 7B shows the binder with small tails 705 and 707 attached to their respective Velcro® fasteners.

The determination factor in the proper fit of a binder is not a person's size but his lung expansion. Inspiration and expiration vary considerably in individuals of the same stature due to differences in age, health, activity, and the physical capacity of their lungs. Many binders which are sized to fit the "small" medium or "large" person do not address the critical issue of lung expansion and may well be too large or too small. Binders with widely spaced Velcro® fasteners allow closure only at fixed intervals that may not match the patient's need.

The present invention, on the other hand, is totally adjustable, since it is sized and cut to fit the individual patient. Velcro® closures may be placed at any point on the circumference of the binder. Predetermined attachment panels no longer dictate binder closure. Rather, the present invention provides limitless patient fit.

The present invention's use of flexible, but relatively inelastic material provides compression around the entire body resulting in superior, equally distributed support. While offering controlled compression, the present invention allows for sudden lung expansion, as in coughing, and the demands of deep breathing therapy.

The binder closing may be diagonally positioned instead of straight. With diagonal closure, fit may be snugger at top and looser at bottom or vice versa; in this way pressure on the upper and lower abdomen may be varied to suit the patient's particular condition. For example, if the incision is in the lower abdomen it may be desirable to have less pressure on that area, while maintaining maximum pressure on the rest of the abdomen.

For graduated fit with an angled closure, pull the appropriate end of the binder to the desired tautness for the snugger fit, then press-close Velcro at that end on a diagonal. As you continue to press-close from top to bottom or bottom to top, the diagonal angle creates a graduated fit which is loosest at the opposite end from which you began. The greater or lesser the angle at which the closure is begun will determine the degree of graduation from snuggest to loosest.

Applying the Binder

The patient should be supine. The patient is measured and the binder cut to fit. Place the binder smoothly under the patient and, using the patient's weight to hold the binder in place, pull both ends 105 and 107 of the binder outward from the body. Pull the ends together until the necessary compression has been reached. Proper tension is the key to getting optimal binder benefit.

Make sure the binder is wrapped around the lower abdomen, comfortably below the diaphragm so that it doesn't interfere with respiration, and fits securely, but not tightly, over the iliac crest.

Press-fasten the Velcro® closure 135 from the bottom of the binder upward in the direction of venous return, adjusting for the desired compression. Properly placed, low enough on the umbilical area to support abdominal muscles. This has the advantage of placing the binder such that the patient may sit down while wearing the binder without the binder cutting into the wound.

Use with Drainage Tubes

The inelastic material of the present invention is designed to accommodate the use of surgical drainage tubes. However, care must be exercised in applying the binder so as not to cause discomfort or irritation to the wound site. Drainage tube occlusion can be prevented by layering surgical sponges on both sides of the drain on the patient's abdomen prior to applying the binder.

If Penrose-type drains are being used, holes should be cut in the binder to accommodate the tubes. Avoid placing the overlapped thickness of the binder over the drainage site. Mark an "X" on the Neoprene® where the hole will be made, crease the material at this point and make an elliptical cut in the material. When the Neoprene® is tensioned, the elliptical cut will become a round hole to accommodate the drain. The diameter of the hole will be equal to the length of the cut. Brush away any loose fibers that have separated from the fabric. The binder will not tear or ravel where a cut has been made.

Care Instructions

In normal hospital use, the present invention requires minimal care. When soiled, it may be machine or handwashed in a mild detergent. Warm or cold water temperature is recommended. Before washing, make sure surfaces are securely fastened to prevent lint from gathering in the Velcro fibers weakening their locking properties. The binder may be hung dry. Binder sterilization is rarely necessary, but gas sterilization may be used if required. There are no special storage requirements.

The flexible relatively inelastic material used by the present invention can be engaged and disengaged an indefinite number of times. Although some distortion may occur, this condition does not compromise the holding power of the invention.

Home Use

Upon discharge from the hospital, patients may take the binder home for continued benefits both during and after recovery. They will find that the binder fits inconspicuously under clothing to provide comfortable support as they engage in normal activity.

The patient may be instructed that self-application is easy, as follows:
1. Position tails 105 and 107 of the invention over the hips and tension the binder.
2. Wrap around
3. Press Velcro section 135 closed.

The binder may also be applied in the same way while lying down.

Clinical Experience

The binder taught by the present invention has been used clinically 110 times with male patients in the following procedures:
  1. Phalloplasty augmentation and phialloplasty enhancement (girth)
  2. Reconstruction of penile surgery.
  3. Scar revisions.
  4. Liposuction of pubic area and abdomen.

The recovery time of these patents has improved by six weeks and their rate of infection has decreased by 40 percent as compared with patients undergoing the same surgical procedures who did not use the present invention.

Clinical Study

The the present invention as taught by FIGS. 5, 6, 7A and 7B was the subject of a clinical study conduced by doctors at the John Sealy Hospital, University of Texas Medical Branch at Galveston, Tex. In this study 300 post-cesarean section women were divided into three groups. 100 patients received the abdominal compressions binder taught by the present invention (called the "Mott binder" after its inventor); 100 patients received conventional prior art cloth elastic binders, and 100 patients received no support garment.

The purpose of the study was to address whether a larger area of support (the approximately 280 degree gentle tension provided by the Mott binder) yields any improvement in the rates of wound hematoma formation, wound separation, infection or improvement in subjective pain scale, or reduced analgesic requirements for the patents.

The result of this study, which is in the process of publication, shows that the use of the present invention is beneficial. Patients who used the present invention had one case of wound separation and no cases of wound infection. Patients who used the prior art cloth elastic binder had eight (8) incidences of wound separation and 11 cases of wound infection. Patients in the control group with no binder had seven (7) wound separation incidences and 10 wound infections.

Pain scale evaluation showed that the Mott binder group reported an average pain designation of six (6) (+/−1.1). This compares to a reported pain designation of eight (8) (+/−1.7) from patients using conventional prior art binders and eight (8) (+/−1.1) reported by patients in the control group that used no binder. This subjective evaluation was confirmed by the fact that patients using the binder taught by the present invention consumed 25% less pain medication (meperidine) than patients in who used the prior art binders and the control group patients who used no binder.

This study also noted that the patients who used the binder taught by the present invention began walking earlier than the patients who used prior art binders or no binder. Elective patient ambulation of the Mott binder patients averaged four (4) hours post-operative, versus six (6) hours in the other two groups.

The conclusion of this study was that ". . . the uniquely designed set of tension in the Mott binder provides tissue support without compromising blood flow to facilitate wound closure with fewer incidences of separation. The reduced incidence of seroma and hematoma formation may provide the mechanism. The reduced rate of wound infection may also be a related or contributing factor. The reduction in subjective pain designation supported by the reduced average requirement of post-operative meperidine seems to be related to the tension and support of the binder . . . "

This study indicates that the present invention provides an effective method of reducing post-operative pain, infection and wound separation. This method is to place a relatively inelastic abdominal binder over the iliac crest of the patient and over the patients abdomen and genital areas such that a mild tension is created between the portion of the binder passing over the iliac crest and the part of the binder passing over the abdomen and genital area, whereby the abdomen and genital areas of the patient are placed in compression.

Although the inventor has described a specific embodiment of his invention in this specification and drawings, these are only illustrative of the invention. The scope of the invention should be limited only be the appended claims and their legal equivalents.

What is claimed is:

1. A medical binder for use on a patient, the patient having an iliac crest and an abdomen, comprising: a generally rectangular sheet of flexible, relatively inelastic material, said sheet having a tail end and a cut-out end, said tail end and said cut-out end being spaced apart by the length of said sheet, said sheet further having a right side curve-shaped cut-out area on a right edge of said sheet proximate said cut-out end of said sheet and a left side curve-shaped cut-out area on a left edge of said sheet spaced apart from said right side curve-shaped cut-out area by a width of said sheet; the shape of said right side curved-shaped cut-out and said left side curved-shaped cut-out being selected such that the binder closely fits the patient during use, said sheet further having its tail end split longitudinally into a right tail and a left tail by a cut through a portion of the length of the sheet, said right tail and said left tail each having a distal end and being sufficiently long and wide to allow said tails to pass over the iliac crest of the patient during use; and said right tail and said left tail having at their distal ends means for affixing the distal end of each of said right and left tails to the cut-out end of said sheet, wherein the binder is held in adjustable compression against the iliac crest and abdomen.

2. A medical binder as in claim 1 wherein said right tail and said left tail are split by a cut along part of their length into a plurality of short tails and said plurality of short tails have at their distal ends means for affixing the distal end of each said short tail to the cut-out end of said sheet, wherein the binder is held in adjustable compression against the iliac crest and against the abdomen.

3. A medical binder as in claim 2 wherein the radius of compression is greater than 180 degrees.

4. A medical binder as in claim 2 wherein the cut-out end of the sheet is provided with a plurality of hook and loop fasteners and the means for affixing the plurality of short tails to the cut-out end of the sheet is a cloth backing on the binder.

5. A medical binder as in claim 4 wherein the cloth backing is terry cloth laid over a relatively non-elastic plastic.

6. A medical binder as in claim 1 wherein the material of the binder is anisotropic with respect to stretching such that it stretches more in the longitudinal direction than in the direction of its width.

7. A medical binder as in claim 1 wherein a plurality of relatively small holes are provided on the portion of the binder that would be proximate the genital area of a female patient.

* * * * *